United States Patent [19]

Niklaus

[11] 4,442,124

[45] Apr. 10, 1984

[54] VALPROIC ACID ESTER WITH ANTIEPILEPTIC AND ANTICONVULSANT ACTIVITY AND PHARMACEUTICAL COMPOSITIONS THEREFROM

[75] Inventor: Zemp J. Niklaus, Vaduz, Liechtenstein

[73] Assignee: Texcontor-Anstalt, Vaduz, Liechtenstein

[21] Appl. No.: 155,588

[22] Filed: Jun. 2, 1980

[30] Foreign Application Priority Data

Jun. 8, 1979 [IT]  Italy ................................. 23392 A/79

[51] Int. Cl.³ ...................... C07C 69/28; A61K 31/22
[52] U.S. Cl. .................................... 424/311; 424/317; 560/263; 562/606
[58] Field of Search ......................... 560/263; 424/311

[56] References Cited

U.S. PATENT DOCUMENTS 3,076,839  2/1963  Webb .................................. 560/248
3,148,207  9/1964  Weinkauff et al. .................. 560/236
3,325,361  6/1967  Meunier ............................... 424/311
3,993,684  11/1976  Dunnawant et al. ............... 560/222

*Primary Examiner*—Vivian Garner
*Attorney, Agent, or Firm*—Bucknam and Archer

[57] ABSTRACT

The compound pivaloyloxymethyl 2-propyl-pentanoate of formula I:

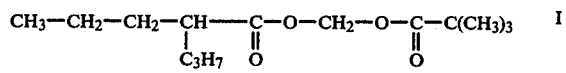

is described. The process for the preparation consists of reacting 2-propyl-pentanoic acid with chloromethyl pivalate and isolating the pivaloyloxymethyl 2-propyl-pentanoate from the reaction mixture. Pharmaceutical compositions with antiepileptic and anticonvulsant activity containing an effective amount of compound I are described.

2 Claims, No Drawings

VALPROIC ACID ESTER WITH ANTIEPILEPTIC AND ANTICONVULSANT ACTIVITY AND PHARMACEUTICAL COMPOSITIONS THEREFROM

The present invention relates to novel compositions of matter useful against epilepsy and convulsions and specifically to novel esters of 2-propyl-pentanoic acid. More specifically, the present invention relates to pivaloyloxymethyl 2-propyl-pentanoate of formula I

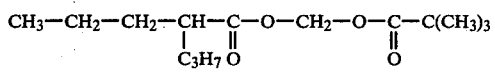

It is well-known that 2-propyl pentanoic acid which is also called valproic acid, is an agent used against epilepsy and against convulsions, which acts by a physiological mechanism as a metabolic inhibitor on the binding sites of the enzyme which catalyzes the deactivation of γ-aminobutyric acid (GABA), with the result that the brain levels of GABA are increased and this action results in a biochemical control on the mechanisms which give rise to the epileptic crisis.

It is also well-known, however, that valproic acid is not absorbed in a uniform manner through the intestine because of the free carboxyl group which is partially in the ionized form.

Several attempts have been made in the past for the purpose of modifying the molecule of valproic acid by preparing the sodium salt or the amide, but they have not provided the solution to the problem of achieving uniformity of enteric absorption.

Many efforts have been made also for the purpose of improving the pharmaceutical formulation because the lack of uniformity of absorption is due to the ionizable polar group of the carboxylic acid, a feature which is inherent in the structure of valproic acid. However, also these efforts have been unsuccessful.

It has now been found unexpectedly, that pivaloyloxymethyl 2-propyl-pentanoate, also called pivaloyloxymethyl valproate, the compound of formula I, exhibits high anti-epileptic and anti-convulsant activity at the same level of valproic acid, but at the same time, is characterized by a markedly greater absorption. Further, the absorption occurs more rapidly and it is more uniform.

The crux of the present invention resides in the preparation of the novel compound of formula I which exhibits high anti-epileptic and anti-convulsant activity and which also exhibits high absorption, rapid absorption and more uniform absorption.

Another object of the present invention resides in providing pharmaceutical compositions, exhibiting anti-epileptic and anti-convulsant activity which contain as the activity ingredient, the ester of valproic acid of formula I.

A further object of the present invention is to provide a method for the preparation of pivaloyloxymethyl 2-propyl-pentanoate.

In accordance with the process of the present invention, 2-propyl-pentanoic acid of formula II is reacted with chloromethyl pivalate of formula III, preferably in the presence of an acid acceptor in accordance with the reaction scheme hereinbelow.

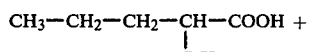

(II)

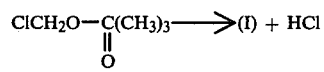

(III)

As acid acceptor, it is possible to use a inorganic base for instance, an hydroxide, carbonate or bicarbonate of alkali or alkaline earth metals or an organic base such as for instance, a tertiary amine.

The example which follows illustrates the process according to the present application.

EXAMPLE

In a three-neck flask provided with a stirrer, thermometer, and a reflux condenser are placed 36.77 g (0.255 mole) of valproic acid dissolved in 1 liter of acetone. To the solution, 35 grams of $K_2CO_3$ are added and subsequently under stirring 39.15 grams (0.260 mole) of chloromethyl pivalate. The reaction mixture is warmed under reflux for five hours, cooled and poured under stirring in 2 liters of water kept at the temperature of about 5° C. An oily material separates, which is removed, dissolved into 200 cc of ethyl acetate, washed twice with a saturated bicarbonate solution, using a 50 cc portion each time and twice with water using a 50 cc portion each time. The product is dried over anhydrous sodium sulfate. The solvent is then evaporated and the colorless oil is distilled under vacuum at a pressure of 0.5–1.0 mm of mercury. The fraction which boils at 143°–150° C. is collected.

The elementary analysis and spectrographic data (IR, NMR) confirm the structure of the product, which is soluble in alcohols, ethers, ketones, insoluble in water. The pharmacological and toxicological properties of the product of formula I, defined hereinbelow with the symbol PEV are illustrated hereinbelow.

1. Acute toxicity

The acute toxicity of PEV has been investigated on Swiss albino mice of about 20 grams average weight and in Wister rats of 150±10 grams average weight by administration both through the oral route and by the endoperitoneal route.

All the animals fasted beginning 12 hours before the experiment. For the experiment, there are used 10 animals that is 5 males and 5 females for each dosage level of treatment. The values of $DL_{30}$ are expressed in mg/kg and are calculated on the basis of the mortality which has been determined within 8 days after the administration in accordance with the method of Lichtfield and Wilcoxon. The results are tabulated hereinbelow.

TABLE 1

| Animal species | Route of Administration | $DL_{50}$ mg/kg and range |
|---|---|---|
| Mouse | Oral | 1214 (1109–1327) |
| Mouse | endoperitoneal | 510 (461–557) |
| Rat | Oral | 1438 (1327–1562) |
| Rat | endoperitoneal | 608 (502–716) |

The values which have been obtained are overlapping with data known in the literature for valproic acid, that is 2-propyl-pentanoic acid; actually in one case, that is the rat by the oral route, the value of PEV of 1438 mg/kg is substantially greater than the value reported in the Merck Index, 9th Edition, page 1273, No. 9574 where the $DL_{50}$ in mg/kg is reported to be 670.

(2) Enzymatic hydrolysis in vitro

The hydrolysis is carried out with a pool of blood of livers removed from six rats. In the case of livers, one operates with a homogenous material obtained from one gram of tissue and nine cc of buffer of pH 7 (16.45 cc of 0.2 M $Na_2HPO_4$ and 3.53 cc of 0.1 M of citric acid.)

The ester of formula I is dissolved in ethyleneglycol in the ratio of 65:35 (V/V) in the concentration of 10 mg/cc. Aliquots of this solution are added to the blood and to the liver homogenate for the purpose of achieving a concentration of 200 μg of ester per cc of blood or per gram of liver. The incubation is carried out at 37° C. with intervals of 2, 5, 10, 15, 30, 60, 120, and 240 minutes. Each test is carried out in a separate test tube. At the end of the prescribed period, the test tube is immersed in ice. The extraction is carried out in each test tube with small amounts of HCl, 4 cc of 0.33 N $HClO_4$ per cc of incubated blood and 1 cc of n-hexane.

The test tubes are then removed from the ice and are stirred for a period of ten minutes. Centrifugation is carried out for the purpose of separating the phases and the organic phase in n-hexane is directly injected into the gas-chromatographic apparatus.

Recovery from Extraction

The extraction described above has been carried out in all the tests under study. The recovery of the extraction from blood and from liver homogenates is 97% in the case of valproic acid and 99% in the case of PEV.

Pharmacokinetics

The study of plasma levels is carried out on Sprague-Dawley albino rats of an average body weight of 215 grams (200-230). Prior to the experiment, the rats fasted for a period of twelve hours. The acid is administered both orally and intravenously, but the ester alone is administered orally. The administrations are carried out with equimolar doses, that is in the dose of 1.39 millimole/kg which corresponds to a dose of 230 mg/kg in the case of the acid administered as the sodium salt and a dose of 360 mg/kg in the case of PEV. Both the acid as well as the ester are dissolved in ethyleneglycol:ethyl alcohol in the proportion of 65-35 (V/V). The concentration of the solution is calculated in a manner to administer 2 cc/kg. After the intervals of time shown in Table 2 in minutes or in hours, the rats in groups of six, are killed by decapitation, the blood is collected and centrifuged for the purpose of obtaining the plasma which is extracted and analyzed as previously described.

TABLE 2

PLASMA LEVELS OF VALPROIC ACID IN RATS TREATED WITH VALPROIC ACID ADMINISTERED IN THE FORM OF THE SODIUM SALT ORALLY AND INTRAVENOUSLY AND WITH PEV ORALLY IN ALIQUOT DOSES OF 1.39 MMOLES/KG

| Time Intervals | Valproic Acid i.v. ± d.s.** | Valproic Acid Orally ± d.s. | PEV Orally ± d.s. |
|---|---|---|---|
| 15 mins. | $449 \pm 49\ \mu g.ml^{-1}$ | — | — |
| 30 mins. | $172 \pm 17\ \mu g.ml^{-1}$ | $4 \pm 4\ \mu g.ml^{-1}$ | $12 \pm 2\ \mu g.ml^{-1}$ |
| 1 hour | $70 \pm 10\ \mu g.ml^{-1}$ | $11 \pm 8\ \mu g.ml^{-1}$ | $65 \pm 8\ \mu g.ml^{-1}$ |
| 2 hours | $35 \pm 7\ \mu g.ml^{-1}$ | $23 \pm 9\ \mu g.ml^{-1}$ | $44 \pm 5\ \mu g.ml^{-1}$ |
| 3 hours | $24 \pm 3\ \mu g.ml^{-1}$ | $22 \pm 8\ \mu g.ml^{-1}$ | $25 \pm 3\ \mu g.ml^{-1}$ |
| 4 hours | $22 \pm 4\ \mu g.ml^{-1}$ | $20 \pm 8\ \mu g.ml^{-1}$ | $22 \pm 2\ \mu g.ml^{-1}$ |
| 8 hours | $14 \pm 3\ \mu g.ml^{-1}$ | $12 \pm 5\ \mu g.ml^{-1}$ | $14 \pm 2\ \mu g.ml^{-1}$ |
| 14 hours | $7 \pm 1\ \mu g.ml^{-1}$ | $8 \pm 5\ \mu g.ml^{-1}$ | $8 \pm 1\ \mu g.ml^{-1}$ |
| 24 hours | $2 \pm 1\ \mu g.ml^{-1}$ | $2 \pm 2\ \mu g.ml^{-1}$ | $3 \pm 1\ \mu g.ml^{-1}$ |
| AUC* | $479\ \mu g.ml^{-1}hour$ | $239\ \mu g.ml^{-1}hour$ | $374\ \mu g.ml^{-1}hour$ |

*Area Under Curve
**Degree of Dispersion

Results

The results in Table 2 illustrate the plasma levels in rats measured after treatment with the sodium salt of valproic acid orally and intravenously or after the rats have been treated orally with PEV.

The levels are relative with respect to valproic acid because none of the rats treated with the ester have exhibited the presence of PEV in the plasma.

After venous administration, the levels of valproic acid decrease with time with a bioexponential curve.

After oral administration of sodium valproate, as shown in Table 2, the peak is noted about at the two hours period, but the values present a substantial dispersion. After administration of PEV, the peak is observed after one hour and the dispersion of the data is substantially less than the data which are observed after oral administration of sodium valproate, while the dispersion of plasma values after administration of PEV and after administration intravenously of the sodium valproate are about in the same range.

The peak of plasma levels after administration of PEV is reached more rapidly and is greater than the peak observed after administration of sodium valproate orally. On the basis of the areas below the curve of the plasmatic levels, (AUC), it is possible to calculate the absolute biodisponibility, which results 49.9% for sodium valproate and 72.4% for PEV. The difference in biodisponibility between sodium valproate and PEV results in the amount of 45.5% in favor of the ester.

On the basis of the results, it is concluded that PEV is absorbed more rapidly, but even more significant, more uniformly compared with valproic acid. An index of the dispersion of the data has been calculated by determining the standard variation in percent with respect to the average value for each group under examination.

For every type of treatment, the average of this index has been calculated. The following values have been obtained:

Valproic acid, i.v. = 18.3
valproic acid, orally = 60.5

PEV, orally = 15.2

The above data show that the dispersion of the data obtained by administering orally PEV, which gives an average index value of 15.2, is the best, because it results in the same order of magnitude as the dispersion obtained after administration intravenously of valproic acid which gives the value of 18.3, and is one-quarter the value obtained by administering valproic acid orally, which is 60.5.

Also, with respect to the absolute biodisponibility calculated on the basis of the areas under the curve of the plasma levels integrated with the trapezoidal system AUC, PEV gives results superior to the acid.

The results hereinabove show the therapeutic value of the compound in accordance with the present invention which may be effectively used for the treatment of epilepsy in general or the compound may also be used more specifically for the special types of epilepsy known as "petit mal", "grand mal", psycomoter epilepsy and similar conditions. For this purpose, the compound of formula I may be formulated as capsules of 200-400-500 mg or it may be administered in liquid form in a 20% solution in a suitable solvent so that it may be administered in daily doses of 200-2000 mgs depending upon the seriousness of the disease, the age of the patient, and medical prescriptions.

What is claimed is:

1. The compound pivaloyloxymethyl 2-propyl-pentanoate of formula I:

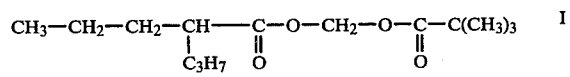

2. A pharmaceutical composition with antiepileptic and anticonvulsant activity containing as the active compound an effective amount of pivaloyloxymethyl 2-propyl-pentanoate and a pharmaceutically acceptable carrier.

* * * * *